(12) United States Patent
Docherty et al.

(10) Patent No.: US 7,693,580 B2
(45) Date of Patent: Apr. 6, 2010

(54) RADIANT THERAPEUTIC WRIST HEATING PAD

(75) Inventors: Francis G. Docherty, Calgary (CA); Wendy Docherty, Calgary (CA); John W Crerar, Calgary (CA)

(73) Assignee: CT Investments Ltd., Calgan (CA)

( * ) Notice: Subject to any disclaimer, the term of this patent is extended or adjusted under 35 U.S.C. 154(b) by 1219 days.

(21) Appl. No.: 11/051,086

(22) Filed: Feb. 4, 2005

(65) Prior Publication Data

US 2006/0052855 A1 Mar. 9, 2006

Related U.S. Application Data

(63) Continuation-in-part of application No. 10/934,158, filed on Sep. 3, 2004.

(51) Int. Cl.
*A61N 5/00* (2006.01)
(52) U.S. Cl. .................. 607/98; 607/99; 607/100
(58) Field of Classification Search .............. 607/104, 607/108–112
See application file for complete search history.

(56) References Cited

U.S. PATENT DOCUMENTS

| | | | |
|---|---|---|---|
| 2,850,009 | A | 9/1958 | McElwee |
| 2,949,108 | A | 8/1960 | Vecchio |
| 3,751,620 | A | 8/1973 | Yuasa et al. |
| 3,885,553 | A | 5/1975 | Vecchio |
| 4,186,294 | A | 1/1980 | Bender et al. |
| 4,221,954 | A | 9/1980 | Cohen |
| 4,334,541 | A | 6/1982 | Leist et al. |
| D273,517 | S | 4/1984 | Medlin et al. |
| 4,507,816 | A | 4/1985 | Smith, Jr. |

(Continued)

FOREIGN PATENT DOCUMENTS

WO WO-99/62302 A1 12/1999

OTHER PUBLICATIONS

Office Action issued on Jun. 19, 2009 in Chinese Application No. 200580036501.4.

(Continued)

*Primary Examiner*—Roy D Gibson
(74) *Attorney, Agent, or Firm*—Venable LLP; Ralph P. Albrecht; Zayd Alathari

(57) ABSTRACT

A radiant therapeutic wrist heating pad, which is not hot to the touch, provides substantial infrared radiation to a user's wrist to alleviate symptoms of carpal tunnel syndrome. It can be used for extended periods without feeling uncomfortable to the skin, while imparting deep therapeutic heat to the user's wrist. The heating pad is comprised of a radiant heat generating layer having a plane surface comprising means for radiating heat evenly from its surface, a pair of flexible electrically insulating and radiation permeable layers located adjacent and covering opposite sides of the layer, a thermal insulation layer disposed against and covering one of the electrically insulating layers, and a sealed radiation permeable envelope enclosing the entire heater. Preferably the flexible heat generating layer is comprised of a fiberglass material impregnated with a resistive material, which material provides a surface temperature, when current is conducted therethrough, which is no greater than about 54 degrees Celsius. Current limiting thermostats are provided to prevent energy and temperature spikes in the event that any of the electrical components are creased or bent. A stiffening element helps protect the electrical components, and also orients the user's hand with respect to the forearm so as to place the wrist in a therapeutic position.

14 Claims, 6 Drawing Sheets

U.S. PATENT DOCUMENTS

| | | |
|---|---|---|
| D279,818 S | 7/1985 | Douglas |
| 4,563,843 A * | 1/1986 | Grether et al. ............... 52/172 |
| 4,607,624 A | 8/1986 | Jefferson |
| 4,700,054 A | 10/1987 | Triplett et al. |
| 4,888,472 A | 12/1989 | Stitz |
| 5,074,285 A | 12/1991 | Wright et al. |
| 5,151,578 A | 9/1992 | Phillips et al. |
| 5,324,911 A | 6/1994 | Cranston et al. |
| 5,371,340 A | 12/1994 | Stanfield |
| 5,674,423 A | 10/1997 | Wright, Sr. |
| 5,686,005 A | 11/1997 | Wright, Sr. |
| 5,841,944 A | 11/1998 | Hutchinson et al. |
| 6,006,136 A * | 12/1999 | Glucksman ............... 607/98 |
| 6,067,404 A | 5/2000 | Wilkins et al. |
| 6,108,581 A | 8/2000 | Jung |
| 6,185,742 B1 | 2/2001 | Doherty |
| 6,188,051 B1 | 2/2001 | Kusek |
| 6,254,922 B1 | 7/2001 | Reichelt |
| 6,261,261 B1 | 7/2001 | Gordon |
| 6,263,158 B1 | 7/2001 | Rutherford |
| 6,294,758 B1 | 9/2001 | Masao et al. |
| 6,297,481 B1 | 10/2001 | Gordon |
| 6,329,638 B1 | 12/2001 | Bloodworth |
| 6,392,206 B1 | 5/2002 | Von Arx et al. |
| 6,392,208 B1 | 5/2002 | Arx |
| 6,432,344 B1 | 8/2002 | Eckman et al. |
| 6,433,317 B1 | 8/2002 | Arx et al. |
| 6,434,328 B2 | 8/2002 | Rutherford |
| 6,510,346 B2 | 1/2003 | Gordon |
| 6,516,229 B1 * | 2/2003 | Wey ............... 607/100 |
| 6,517,501 B1 * | 2/2003 | Slautterback ............... 602/5 |
| 6,519,835 B1 | 2/2003 | Von Arx et al. |
| 6,539,171 B2 | 3/2003 | Von Arx et al. |
| 6,554,787 B1 | 4/2003 | Griffin et al. |
| 6,664,512 B2 | 12/2003 | Horey et al. |
| 6,689,994 B2 | 2/2004 | Reichelt |
| 6,744,978 B2 | 6/2004 | Tweedy et al. |
| 6,748,646 B2 | 6/2004 | Von Arx et al. |
| 2002/0169398 A1 | 11/2002 | Hancock |
| 2004/0143199 A1 | 7/2004 | Cotterell-Grant et al. |

OTHER PUBLICATIONS

Extended European Search Report issued Jan. 22, 2010 for European Application No. 05783464.0.

Machine Translation of WO99/62302 from the EPO website, accessed Jan. 27, 2010.

English Language Abstract of WO99/62302 from the EPO website, accessed Jan. 27, 2010.

* cited by examiner

RADIANT THERAPEUTIC WRIST HEATING PAD

CROSS REFERENCE TO RELATED APPLICATION

This application is a continuation-in-part of Applicant's corresponding application Ser. No. 10/934,158, filed Sep. 3, 2004, which application is hereby incorporated by reference herein.

BACKGROUND OF THE INVENTION

1. Field of the Invention

This invention relates to an improved heating pad that has been found to be useful for therapeutic applications, and more particularly to an improved radiant therapeutic heater.

2. Description of the Prior Art

Certain types of painful conditions of the muscles or joints such as arthritic pain often have the application of heat prescribed to relieve the pain. Heat is normally applied in a variety of ways, for instance by the use of irritant rubbing compounds which cause local stimulation of blood vessels thereby increasing body heat carried to the location, the use of infrared lamps, the use of radio frequency apparatus such as diathermy machines, the use of hot water bottles or electrically operated heating pads.

While some or all of the aforenoted apparatus is alleged to work to some degree, all have certain disadvantages. For instance, the prolonged use of an infrared heating lamp can cause localized burning of the skin. Diathermy machines are specialized apparatus that require expensive skilled operators. Irritant rubs, while apparently generating local heat, sometimes irritate the skin. Hot water bottles maintain an uneven temperature with time, generally are applied too hot to the skin, and later cool to an ineffective temperature. They are thus uncomfortable for most of their time of application.

A common malady for which heat has heretofore not been generally applied is carpal tunnel syndrome, which generally occurs when tendons or ligaments in the wrist become enlarged, often from inflammation after being aggravated. The narrowed tunnel of bone and ligaments in the wrist pinches the median nerve on the palm side of the wrist, nerves that reach the fingers and the muscles at the base of the thumb. This can result in pain, weakness or numbness in the hand and wrist, often radiating up the arm. Carpal tunnel syndrome can be the result of a combination of factors that increase pressure on the median nerve and tendons in the carpal tunnel, rather than a problem with the nerve itself. While the disorder tends to be congenital—the carpel tunnel is smaller in some people than others—other contributing factors include trauma or injury to the wrist that cause swelling. Some cases are due to work-related cumulative trauma of the wrist. Although in some cases no particular cause can be identified, it is generally believed that repetitive and forceful movements of the hand and wrist during work or leisure activities can cause carpal tunnel syndrome.

Carpal tunnel syndrome is generally treated by immobilizing the wrist in a splint to minimize or prevent pressure on the nerves. Medication to reduce inflammation may also be prescribed. In extreme cases, a surgical procedure is preformed in which doctors open the wrist and cut the ligament at the bottom of the wrist to relieve the pressure. When using a splint or brace, the user's hand is caused to be placed in a preferred position, with the hand bent at the wrist to relieve pressure on the median nerve. The brace can also provide an additional benefit in that the skin temperature of the user the may become slightly elevated and thus provide heat to the user's tendons and ligaments.

What is needed is a brace or splint that can properly position a user's hand with respect to their forearm to alleviate carpal tunnel syndrome symptoms.

It is therefore an object of the present invention to provide a carpal tunnel syndrome therapy wrist brace, which brace properly positions the user's wrist while also having a radiant heat therapy unit for decreasing inflammation.

It is a further object of the present invention to provide a method of treating repetitive strain injuries such as carpal tunnel syndrome.

It is a still further object of the present invention to provide a non-invasive system for the temporary relief of pain associated with repetitive strain injuries.

SUMMARY OF THE INVENTION

The present invention is directed to a novel form of electrically operated heating pad designed specifically for use about a person's wrist to alleviate symptoms common to carpal tunnel syndrome. The invention, in general, is a radiant therapeutic heater comprising a radiant heat generating layer having a plane surface comprising means for radiating heat evenly from its surface, a pair of flexible electrically insulating and radiation permeable layers located adjacent and covering opposite sides of the layer, a thermal insulation layer disposed against and covering one of the electrically insulating layers, and a sealed radiation permeable envelope enclosing the entire heater. The flexible heat generating layer is comprised of a foam insulation layer impregnated with a resistive material, which material provides a surface temperature, when current is conducted therethrough, which is in the range of about 54 degrees Celsius. The heating pad of the present invention may also include a stiffener to protect the heating element from damage due to bending or creasing of the pad. The stiffener preferably has a slight curve so as to position the hand and wrist at a preferred therapeutic angle.

BRIEF DESCRIPTION OF THE DRAWINGS

A better understanding of the invention and various other objects, features and advantages of the present invention will become readily apparent by reading the following description in conjunction with the drawings, which are shown by way of example only, wherein.

DESCRIPTION OF THE PREFERRED EMBODIMENTS

Figure 1:
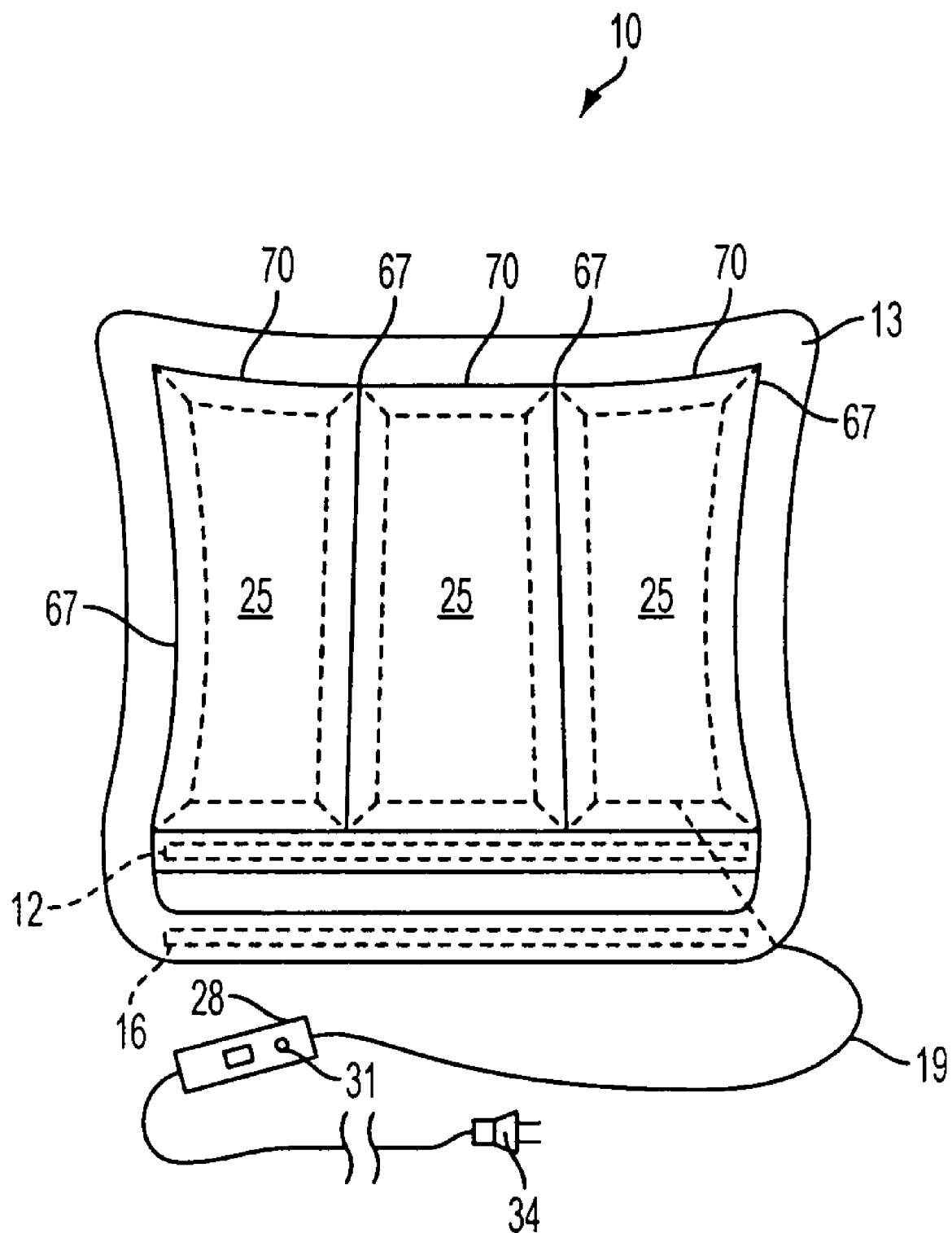
FIG. 1 is a perspective view of a radiant heating pad.

Referring now to the drawings in detail, wherein like reference characters refer to like elements, there is shown in FIG. 1 a perspective view of a radiant heating pad 10 described in applicant's co-pending application Ser. No. 10/934,158. The heating pad 10 preferably has a cloth cover 13 of cotton or other natural fiber, formed into an envelope and closed by a zipper, preferably a hook and loop fastener (Velcro) 16. A power cord 19 extends from an opening which is closed, such as by a second Velcro zipper 22, for carrying current to one or more heating elements 25 which is controlled by an inline cord on-off switch 28 with indicator light 31. While a standard 110 volt AC main plug 34 is shown at the end of power cord 19, it should be noted that upon appropriate design of the heating element 25, other potentials can be used, for instance 12 volts AC or DC, 75 volts AC or DC. Also, the source of electrical power may be a re-chargeable battery pack (not shown) for enhanced portability of the heating pad 10.

Preferably, the surface temperature of the pad is no higher than about 54 degrees Celsius and in the most preferred embodiment on the order of about 49-54 degrees Celsius. As is common with conventional heating pads, the on-off switch 28 may incorporate a variable temperature control. Even at the 54 degrees Celsius temperature the heating pad 10 is safer for application to the skin of the user, while it has been found that the infrared radiation provided by the device of the present invention still penetrates deeply into the body and muscle of the user for the desired therapeutic benefit of the heating pad. Consequently the heating pad 10 can be used in place for even more extended periods of time with a comfortably warm feeling, and without causing surface skin burns.

Figure 2:
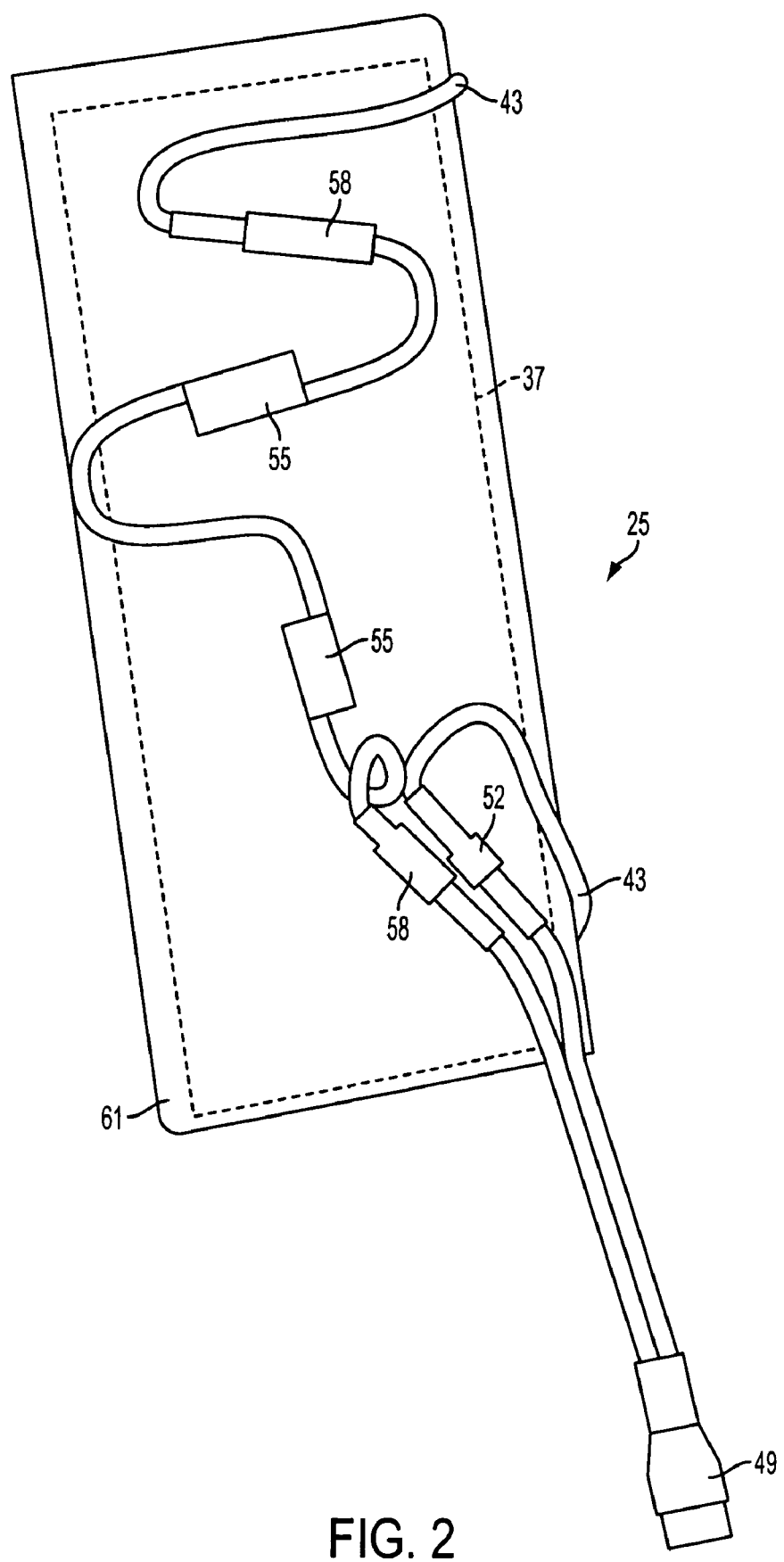
FIG. 2 is a detailed view of a radiant heating element for the heating pad shown in FIG. 1.
Figure 3:
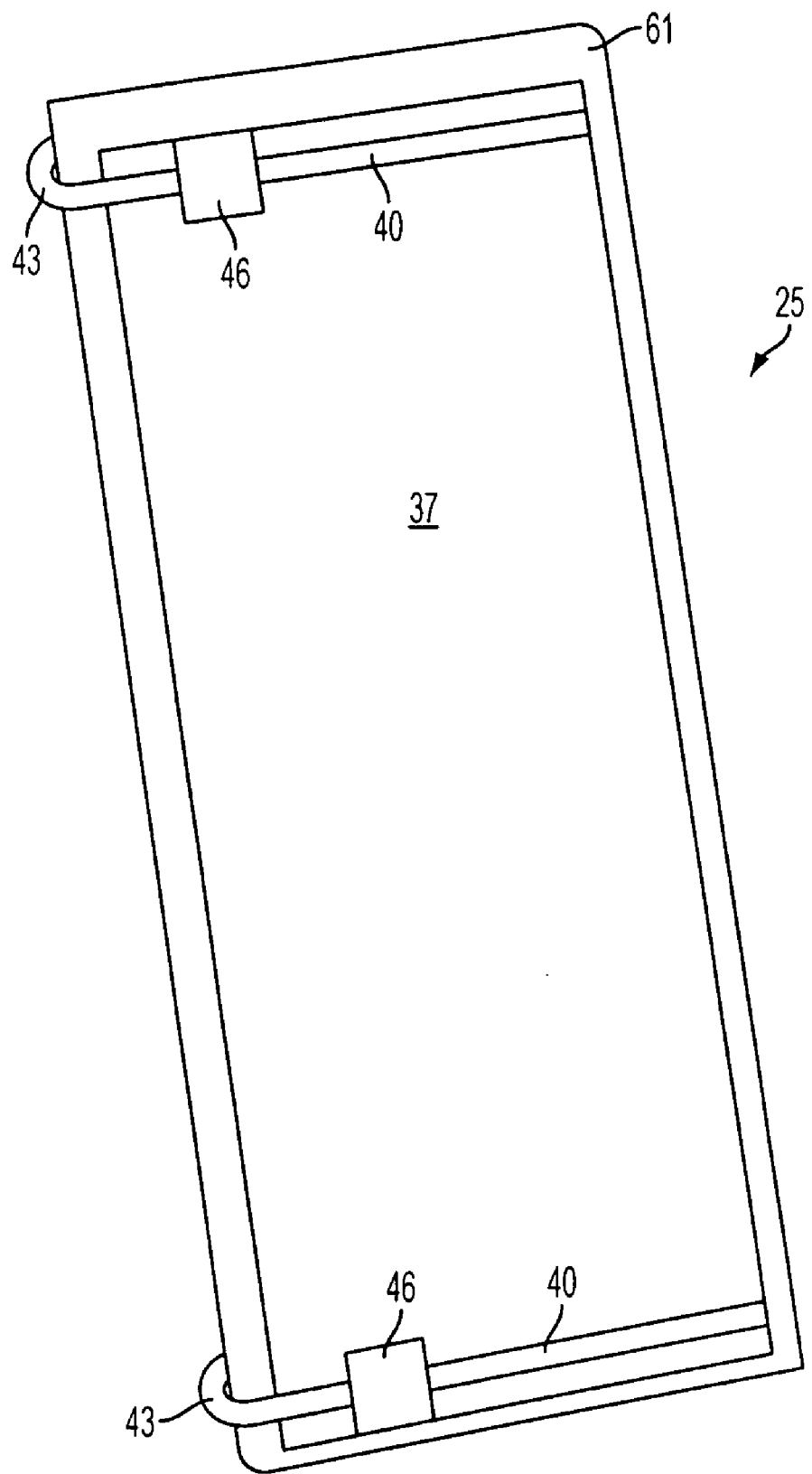
FIG. 3 is a plan view of the reverse side of the radiant heating element of FIG. 2 showing the heat generating layer.

FIGS. 2 and 3 show an embodiment of a heating element 25, which is used within the heating pad 10. The heating element 25 includes of a fiberglass mat or layer 37. The fiberglass layer 37 is preferably thoroughly impregnated and saturated with a chemical compound, which is a mixture of low and high resistance carbon to provide the required resistance. Saturation is carried out in such manner as to insure that the fiberglass is thoroughly covered inside and out homogeneously. Following saturation the material is passed through a series of steel rollers which remove the excess wet chemical, after which it is passed through an oven drying process and is finally subjected to heat of about 425 degrees Celsius to extract any remaining moisture in the material, thus stabilizing the carbon-graphite impregnated material. The coating materials of the kind preferred to be used in the heating element of this invention are described in U.S. Pat. No. 3,865, 626, issued Feb. 11, 1975.

The quantity of the material impregnated in the fiberglass, which forms a resistive layer, ranges from about 0.1 grams per square meter to about 3 grams per square meter. After heat treatment, drawing and passing of the fiberglass through the rollers (the latter of which gauges the thickness of the particles of the impregnate adhering to the material) sets the resistivity of the material.

It should be noted that materials other than fiberglass could be used as a base for the resistive material. For instance, as described in U.S. Pat. No. 3,865,626, a polyester film is treated with a solvent or swelling agent. Electroconductive particles, preferably carbon black is applied to the treated surface in a concentration corresponding to the desired resistance. The film is then subjected to heat treatment to solidify and retain the resistive material in the surface. It should be noted that since the resistance material is basically fabricated of carbon compound, the heating element 25 is a black body radiator, which has a high efficiency of radiant heat dispersion which, it is believed, contributes to the effectiveness of the invention.

Conductive tapes 40, preferably of copper foil, are sewn into electrical contact with the resistive material along parallel edges of the fiberglass layer 37. The tapes 40 can be made of either woven or non-woven material. A pair of wires 43 are then electrically connected to the tapes 40, such as by a clip 46. The other ends of the electrical wires 43 are operatively connected to a quick connector 49, which is connected to a complementary connector (not shown) to individually connect each heating element 25 to the main power cord 19.

It should be noted that as the resistivity of the material 37 is measurable in ohms per square units, the material could be made in large sheets or rolls, and then cut to the required resistance. In the preferred embodiment, the heat element dissipates 26.3 watts per square foot with an input voltage of 110 volts AC. Depending on the specific design, however, the dissipation can be made as low as thirteen (13) watts per square foot. The individual heating elements 25, and thus the overall heating pad 10, can be made a variety of desired dimensions in length or width depending on how and where the heating pad is to be used on a particular body art of the user. For example, "dedicated" heating pads can be designed for use on a users wrist, shoulders, knees or thighs and can be made so as to have securing straps for holding the heating pad in place for the best therapeutic effect. Moreover, although three (3) heating elements 25 are shown in FIG. 1, a larger, single heating element can be used, as well as one or more smaller units.

As shown in FIG. 2, each wire 43 is individually connected to the quick connector 49 and one of the conductive tapes 40 in order to complete the electrical circuit. One of the wires is connected to the quick connector 49 via a second quick connector 52. The other wire is connected to a second quick connector 58 via one or more current limiting thermostats 55. In the preferred embodiment, two (2) thermostats 55 are used, one acting as a back-up in the event of failure of the other. Connected in series with the heating element 25, the thermostats 55 cut off power thereto in case the temperature becomes excessive. The thermostats 55 are preferably connected to the wire 43 and quick connector 49 via a pair of in-line quick connectors 58 for ease of replacement. Thus at least one current limiting control thermostat 55 is within the electrical circuit of the heating element 25 and distributed to sense whether any hot spots may be developing due to a fold, or the like in the heating pad 10.

In order to prevent the wires 43 and/or the thermostats 55 from being inadvertently creased or bent, which may cause a power surge within the heating element 25, these components are attached to a stiffening member 61. Preferably, the stiffening member 61 is a relatively thin layer of propylene material of about three-sixteenths (3/16) of an inch thick. Disposed against the surface of the stiffening member 61 against the thermostats 55 is an insulating layer (not shown) to more fully protect the individual components of the heating element 25. The insulating layer is preferably made of a foam insulation of between about one-quarter (¼) and one (1) inch in thickness, and most preferably the insulation is 1 inch thick.

Additionally, each of the heating elements 25 is preferably encased within a vinyl envelope (not shown) so that only the quick connector 49 protrudes therefrom. In the event that a new heating element is required, the other cover 13 is opened and the quick connector is merely disconnected. A new heating element can then be connected, inserted into the cover 13, and the Velcro zippers 16,22 resealed. This envelope holds all of the above-described elements in a laminated position, and protects them against the intrusion of moisture or other contaminants. The pair of wires 43, which contact the conductive tapes 40 via the clips 43, of course extend through a hole (not shown) in the vinyl envelope, which hole is preferably sealed against the wires 43. Alternatively, the quick connector 49 itself can be a sealed connector projecting from the vinyl envelope, if desired. The area between the zippers 16,22 holds the various wires and connectors for the heating elements 25.

As shown in FIG. 1, the outer cloth bag or cover 13 encloses each vinyl envelope and hence each heating element 25. Preferably the cloth cover 13 is fabricated of terry towel, or other cotton or natural fiber material, which has been found to be most comfortable to the user. As noted above, the cloth cover 13 can be closed by one or more fastening devices, such as by a hook and loop closure zippers (generally referred to as Velcro) or the like. The cover 13 may thus be removed and washed as desired. In a preferred embodiment each half of the cover 13 is stitched 67 together so as to create one or more individual pockets 70 into which each heating element 25 is inserted. This also allows the heating pad 10 to be bent along the area of the stitching 67 to conform to the body part of the user, while each heating element 25 is prevented from being creased by the stiffener 61. The thermostats 55 further prevent temperature spikes in the event that any of the electrical wires or cords are creased or bent.

In operation, the heating pad 10 is plugged in or otherwise connected to a source of electrical current. The heating pad 10 is placed over a region to be therapeutically warmed with deep heat. Current passes through the resistance material of the fiberglass layer 37, creating a source of black body infrared radiation. The radiation is received by the body of the user, and penetrates deeply beneath the skin to the users underlying muscle. Yet the heating pad 10 does not feel uncomfortably hot to the touch as it does not exceed 54 degrees Celsius (140° F.), and preferably about 49-54 degrees Celsius (120-130° F.).

Figure 4:
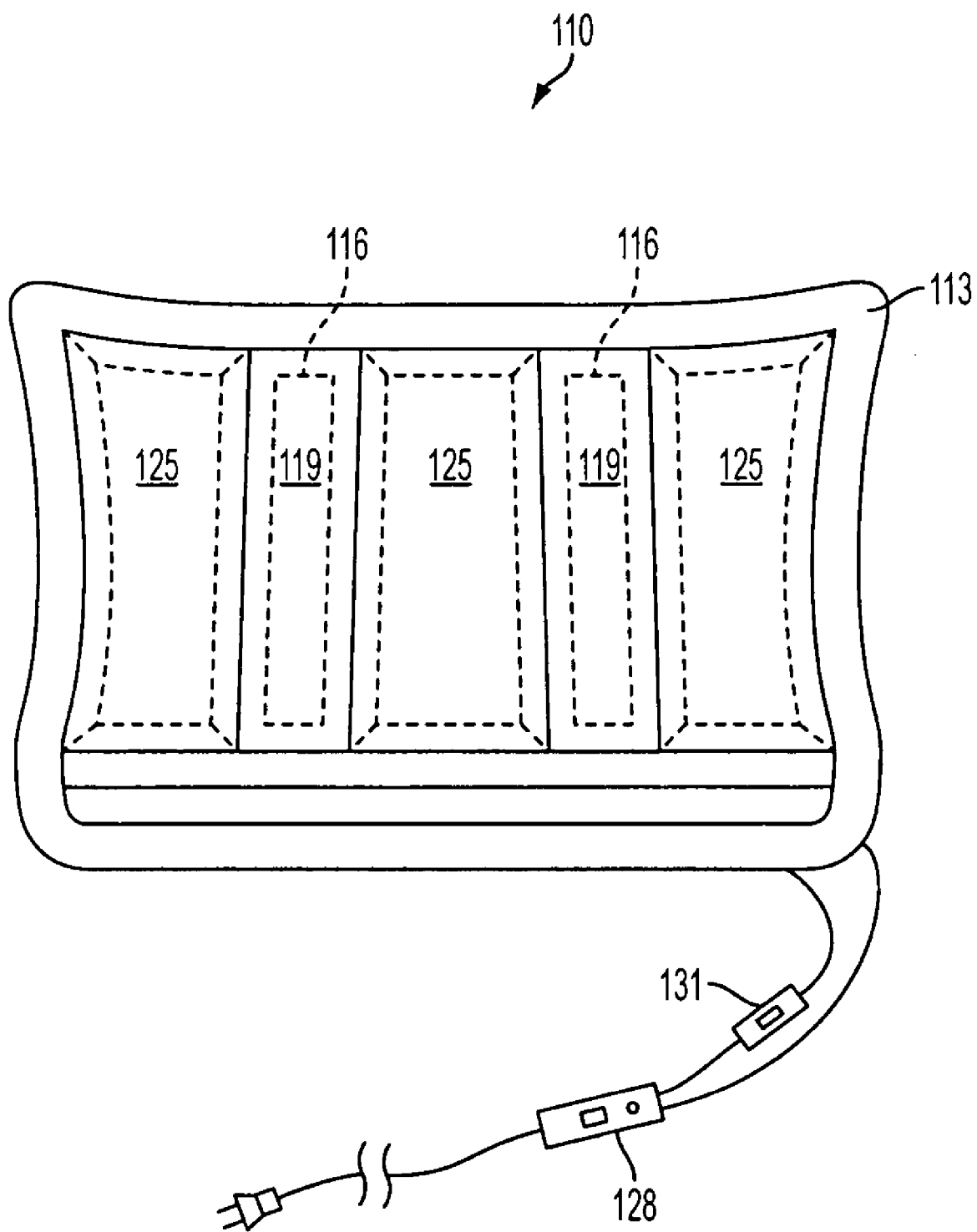
FIG. 4 is a perspective view of a second embodiment of the radiant heating pad.

FIG. 4 shows an alternate embodiment of a vibrating heating pad 110. In this embodiment, the cover 113 includes one or more pockets 116 which house vibrating elements 119 for providing this added therapeutic benefit to the user. Similar to that of the heating elements 125, each vibrating element 119 is connected to a switch 128 which preferably has separate a control 131 for each of the heating elements 125 and vibrating elements 119. As with the heating pad 10, the control 131 for the vibrating elements 119 may include variable speeds.

In the event the heating pad 110 is heated before being applied to the user's body, should the heating pad have a resistivity, which raises its temperature higher than that of the temperature of the human body, the pad may feel warm for an instant when it is first applied to the body of the user. However it has been found that this warmth is almost instantly dissipated by the skin of the user, and further contact with the pad does not impart an uncomfortably hot sensation to the touch. Accordingly there is a very little heat conduction from the inventive structure, but there is substantial radiated heat. The radiated heat is received by receptive bodies opposite the side of the foam pad. Yet the air that is in contact with the heating pad does not heat, since it is transparent to infrared radiated heat.

It has been found that the described structure radiates heat in the wavelength band of between 9 and 12 microns, while the entire infrared bandwidth extends between 0.72 and 3100 microns. It is believed that the particular bandwidth of the radiation which is emitted by this invention contributes to the apparent deep penetration and therapeutic effect obtained.

Figure 5:
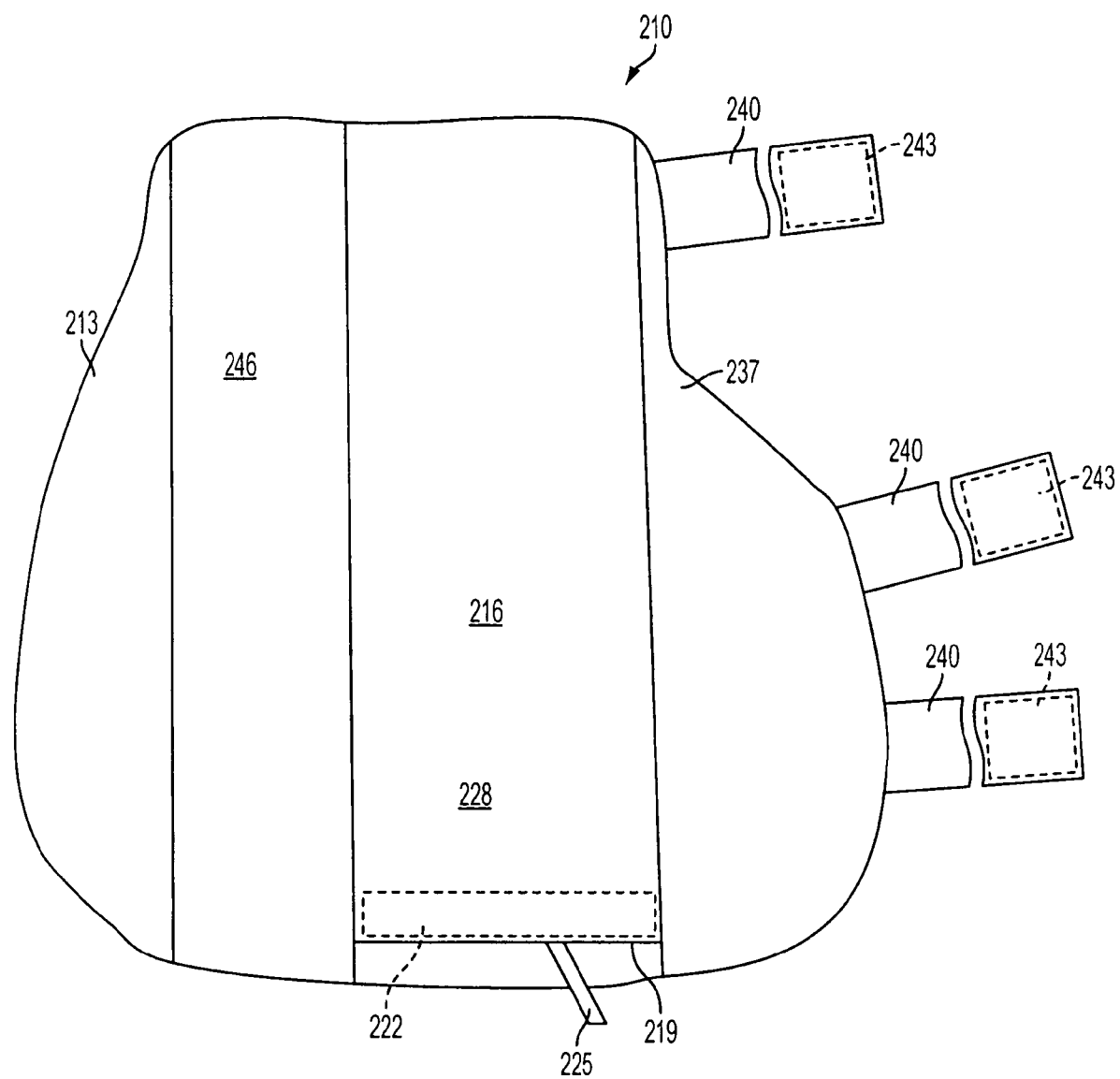
FIG. 5 is a perspective view of a wrist radiant heating pad according to the present invention.

As noted earlier, the radiant heating pad can be made of various sizes, such as the sizes given by the example above, blanket size, or of particular shape to match the shape of a portion of a user's body. Accordingly, FIG. 5 shows a wrist radiant heating pad according to the present invention designed to alleviate symptoms commonly associated with carpal tunnel syndrome.

The wrist radiant heating pad 210 includes a cloth cover 213 of cotton or other natural fibers, forming a pocket 216 having an opening 219, which preferably is closed by a Velcro zipper 222. A power cord 225 extends from the opening 219 and is operatively connected between a radiant heating element 228 enclosed within the pocket 216 and a source of electric power. The heating pad 210 is preferably controlled by an in-line cord and an "on-off" switch with an indicator light, similar to that shown in FIG. 1. The connection to a power source maybe through an electrical outlet plug (not shown) or to a battery pack (not shown).

The design of the wrist radiant heating pad 210 allows it to be wrapped about a user's wrist on either the right or left arm, with the user's thumb being positioned adjacent the angled portion 237. The pad is then wrapped about the user's arm adjacent the wrist, and secured in place by one or more, preferably three, flexible straps 240. The end 243 of each strap 240 is secured to an opposite portion 246 of the pad 210 by Velcro fasteners. Preferably, the strap end(s) 243 includes the hook portion while the opposite portions 246 include the loop portion of the Velcro so as to snugly and properly fit the heating pad 210 to the user's wrist, such that the heating element 228 is positioned so as to provide the optimum therapeutic benefit to the user.

Figure 6:
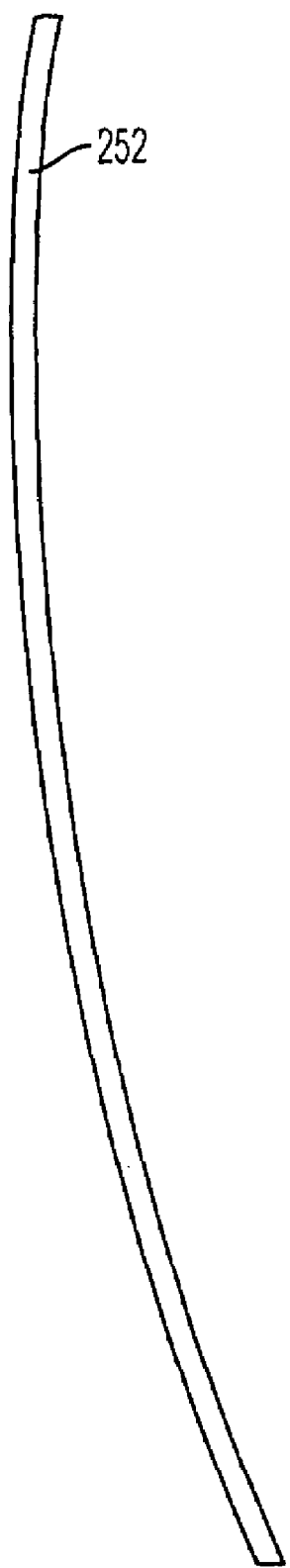
FIG. 6 is a detailed view of a stiffening member according to an embodiment of the present invention.

As described in Applicant's co-pending application the heating element 228 includes a fiberglass mat or layer 249 having the desired resistive properties generally shown in FIGS. 2 and 3. However, for the present invention the stiffening member 252 is curved so as to put the user's wrist in the proper position to alleviate the pinch on the median nerve, and thus provide the preferred therapeutic benefit to the user. As shown in more detail in FIG. 6, the stiffening member 252 is preferably curved at an angle of about +/−5 degrees, with the convex side adjacent the user's forearm. Although it can be of any dimension, the heating element is approximately 2×8 inches, such that the heating pad fits comfortably on the user's inside forearm and wrist.

In order to treat the symptoms typically associated with repetitive strain injuries such as carpal tunnel syndrome, the following method may be used. The heating pad 210 of the present invention is fitted against the user's inside forearm and wrist and the straps 240 adjusted for a comfortable fit. The curve of the stiffening member 252 helps orient the effected area in a predetermined therapeutic position. Electrical power is provided to the device and the radiant heating element 228 is energized. The heating pad 210 is applied to the effected area for a predetermined amount of time, such as about 30-45 minutes as may prescribed by the user's doctor or physical therapist. Because of the design of the present invention, it can be used either in the home or the user's workplace while the user engages in his or her normal activities. Preferably, the user treats the effected area for at least two (2) treatment sessions per day, again as prescribed by a doctor or therapist. The radiant heating of the user's forearm and wrist increases blood flow to the nerves that control pain and hand sensation to relieve pain and numbness. In this manner, the radiant therapeutic wrist heating pad 210 of the present invention can temporarily reduce the inflammation and alleviate the pain of carpal tunnel syndrome.

Accordingly a heating pad has been invented which has significant advantages over prior art therapeutic heat applying devices. Since the pad gives its deep heat penetration by radiation, with a relatively low surface temperature, skin surface burns do not result from prolonged use. The pad is useable by the patient, and no specialist is required for its application. Nonconductive and virtually entire radiative infrared heat in the range of 9 to 12 microns is imparted to the user, which has been found to result in a penetrating deep heat, which patients have found to be highly successful in relief of symptoms of arthritic pain, etc.

It may now become evident to a person skilled in the art understanding this invention that other materials than the ones described can be substituted for the ones described, and that other embodiments and configurations may now be designed. All are considered within the scope and sphere of the invention, as defined in the appended claims. For example, while the invention has been described as having a single radiant heating element, two or more smaller elements may be used for more localized heating. While specific embodiments of the invention have been shown in the drawings and described in detail, it will be appreciated by those skilled in the art that various modifications and alternatives would be developed in light of the overall teachings of the disclosure. Such changes and modifications may be made without departing from the spirit and scope of the present invention and without diminishing its attendant advantages. Accordingly, the particular arrangements disclosed herein are meant to be illustrative only and not limiting as to the scope of the invention, which is to be given the full breadth of the appended claims and in any and all equivalents thereof.

The invention claimed is:

1. A radiant therapeutic wrist heating pad adapted to fit about a user's wrist comprising:
   (a) a radiant heat generating means comprising a black body radiator operatively connected to a source of electrical energy for radiating energy at a wavelength of from about 9 to about 12 microns which penetrates into a body, wherein a resistivity of the heat generating means provides a surface temperature adjacent to the wrist to be heated which is no greater than 54 degrees Celsius;
   (b) a curved stiffening member for preventing creasing of said radiant heat generating means, said curved stiffening member shaped so as to position the user's wrist in a therapeutic position and wherein said stiffening member is curved at about +/−5 degrees;
   (c) a cloth covering having a pocket for housing said radiant heat generating means;
   (d) a power source for providing power to said heat generating means;
   (e) a thermal insulation layer disposed adjacent to the stiffening member and comprising foam insulation; and
   (f) a variable temperature controller.

2. A radiant therapeutic wrist heating pad as defined in claim 1, wherein said radiant heat generating means comprises a fiberglass material impregnated with resistive material.

3. A radiant therapeutic wrist heating pad as defined in claim 2, wherein the foam insulation is approximately 1 inch in thickness.

4. A radiant therapeutic wrist heating pad as defined in claim 1, wherein said radiant heat generating means further comprises a current limiting thermostat.

5. A radiant therapeutic wrist heating pad adapted to fit about a user's wrist comprising:
   (a) a variable temperature controller and a heat generating element, comprising:
      i. a black body radiator comprising a layer of radiant heat generating fiberglass material homogeneously impregnated with an electrically resistive material, wherein a resistivity of the heat generating element provides a surface temperature adjacent to the wrist to be heated which is no greater than 54 degrees Celsius,
      ii. a pair of electrically conductive tapes fixed in electrical contact with the resistive material along opposite sides of the fiberglass material,
      iii. means for applying electrical current to said conductive tapes,
      iv. a curved stiffening member for preventing creasing of said heat generating means, wherein said curved stiffening member is shaped so as to position the user's wrist in a therapeutic position and is curved at about +/−5 degrees, and
      v. a sealed flexible envelope of radiation permeable material enclosing said heat generating means such that an electrical wire extends from said means for applying electrical current to said conductive tapes and out of the pocket;
   (b) a cloth cover having a pocket for housing said heat generating element such that the electrical wire projects from the pocket;
   (c) a power cord for supplying electrical energy to said heat generating means;
   (d) means for closing the cloth cover wherein the power cord extends therefrom for connection to a source of electrical energy; and
   (e) a switch for energizing the heating pad when connected to the electrical energy source.

6. A radiant therapeutic wrist heating pad adapted to fit about a user's wrist comprising:
   (a) means for generating radiant heat energy comprising a black body radiator and a variable temperature controller;
   (b) a power cord for supplying electrical energy to said radiant heat generating means from a source of electrical energy;
   (c) a switch for activating said radiant heat generating means such that a surface temperature of the heating pad varies from about 49 degrees Celsius to about 54 degrees Celsius;
   (d) a cloth bag for removably enclosing said radiant heat generating means and said vibrating means in a pocket; and
   (e) means for orienting the user's wrist in a therapeutic position comprising a curved stiffening member that is curved at about +/−5 degrees.

7. A radiant therapeutic wrist heating pad as recited in claim 6, wherein said radiant heat generating means comprises:
   (a) a radiant heat generating fiberglass material homogeneously impregnated with an electrically resistive material;
   (b) a pair of electrically conductive tapes fixed in electrical contact with the resistive material along opposite sides of the fiberglass material;
   (c) means for applying electrical current to said conductive tapes;
   (d) a curved stiffening member for preventing creasing of said radiant heat generating means, and for orienting the user's wrist;
   (e) a sealed flexible envelope of radiation permeable material enclosing said radiant heat generating means such that an electrical wire extends from the envelope to said means for applying electrical current to said conductive tapes; and
   (f) means for connecting the electrical wire to the power cord.

8. A radiant therapeutic wrist heating pad as recited in claim 6, wherein the cloth bag is flexible.

9. A method of treating repetitive strain injuries of a user, said method comprising the steps of
  (a) providing a radiant heating pad comprising a black body radiator, a curved stiffening member that is curved at about +/−5 degrees, and a variable temperature controller;
  (b) fining the radiant heating pad about an effected area of the user;
  (c) energizing the radiant heating pad for a predetermined period of time;
  (d) de-energizing the radiant heating pad; and
  (e) repeating the step of energizing the radiant heating pad.

10. A method of treating repetitive strain injuries of a user as recited in claim 9, wherein the predetermined time period is about 30-45 minutes.

11. A method of treating repetitive strain injuries of a user as recited in claim 9, further comprising the step of orienting the effected area of the user in a therapeutic position.

12. A method of treating repetitive strain injuries of a user as recited in claim 11, wherein the predetermined time period is about 30-45 minutes.

13. The radiant therapeutic wrist heating pad of claim 1, wherein said curved stiffening member is curved at about 5 degrees.

14. The radiant therapeutic wrist heating pad of claim 1, wherein said curved stiffening member is curved at about −5 degrees.

* * * * *